United States Patent
MacAllister et al.

(10) Patent No.: US 11,771,704 B1
(45) Date of Patent: *Oct. 3, 2023

(54) METHODS OF USING RHO KINASE INHIBITORS TO TREAT ALZHEIMER'S DISEASE

(71) Applicant: Woolsey Pharmaceuticals, Inc., St. Petersburg, FL (US)

(72) Inventors: Thomas MacAllister, Arlington, VA (US); Sven Jacobson, New York, NY (US)

(73) Assignee: Woolsey Pharmaceuticals, Inc., St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,605

(22) Filed: Feb. 28, 2023

Related U.S. Application Data

(63) Continuation of application No. 17/996,812, filed as application No. PCT/US2021/012588 on Jan. 8, 2021.

(60) Provisional application No. 63/014,272, filed on Apr. 23, 2020.

(51) Int. Cl.
*A61K 31/5513* (2006.01)
*A61K 9/00* (2006.01)
*A61P 25/28* (2006.01)

(52) U.S. Cl.
CPC ........ *A61K 31/5513* (2013.01); *A61K 9/0053* (2013.01); *A61P 25/28* (2018.01)

(58) Field of Classification Search
CPC .......................... A61K 31/551; A61K 31/5513
See application file for complete search history.

(56) References Cited

U.S. PATENT DOCUMENTS

| | | | |
|---|---|---|---|
| 11,311,553 B1 * | 4/2022 | MacAllister | A61K 31/551 |
| 11,642,352 B2 * | 5/2023 | MacAllister | A61K 31/551 |
| | | | 514/218 |
| 2011/0294789 A1 | 12/2011 | Nikolich et al. | |
| 2015/0031683 A1 | 1/2015 | Lingor et al. | |
| 2016/0030666 A1 | 2/2016 | Lozano et al. | |

FOREIGN PATENT DOCUMENTS

WO  2005117896 A1  12/2005

OTHER PUBLICATIONS

Kumar et al., Behavioural Brain Research, 2018, 351:4-16.*
International Search Report received in international application No. PCT/US21/12588, dated Apr. 6, 2021.
Balsis et al., "How to do Scores on the ADAS-Cog, MMSE, and CDR-SOB Correspond?". Nov. 30, 2015, The Clinical Neuropsychologist, http://dx.doi.org/10.1080/1385406.2015.1119312; entire document, especially p. 1 para 1, p. 5, table 1.
Sasaguri et al., APP mouse models for Alzheimer's disease preclinical studies. EMBO J. 2017; 36(17): 2473-2487.
Elliott et al., A role for APP in Wnt signalling links synapse loss with β-amyloid production, Translational Psychiatry. 2018; 8(179).
Couch et al., Increased Dendrite Branching in ABPP/PS1 Mice and Elongation of Dendrite Arbors by Fasudil Administration, Alzheimers Dis. 2010; 20: 1003-1008.
Turk, The Effect of Rho Kinase Inhibitors on Alzheimer's Disease, Dissertation. Arizona State University. May 2017.
Nair and Jacob, A simple practice guide for dose conversion between animals and human, J Basic Clin Pharm. 7(2):27-31 (2016).
Ceyzeriat et al., Learning from the Past: A Review of Clinical Trials Targeting Amyloid, Tau and Neuroinflammation in Alzheimer's Disease. Current Alzheimer Research. 2020; 17: 1-13.
Hamano et al., Rho-kinase ROCK inhibitors reduce oligomeric tau protein. Neurobiology of Aging; 2020: 1-14.
Yu et al., Fausidil improves cognition of APP/PS1 transgenic mice via inhibiting the activation of microglia and shifting microglia phenotypes from M1 to M2. Chin J Cell Mol Immunol. 2017; 33(12): 1585-1593.
Hou et al., Changes in hippocampal synapses and learning-memory abilities in a streptozotocin-treated rat model and Intervention by using fasudil hydrochloride. Neuroscience. 2012; 200: 120-129.
Becker et al., Why do so many drugs for Alzheimer's disease fail in development? Time for new methods and new practices? Alzheimers Dis. 15(2):303-325 (2008).
Kamei et al., 1996a. Evaluation of fasudil hydrochloride treatment for wandering symptoms in cerebrovascular dementia with 31P-magnetic resonance spectroscopy and Xe-computed tomography. Clin Neuropharmacol. 19(5):428-38.
Kamei et al., Effect of fasudil hydrochloride on wandering symptoms of c cerebrovascular dementia patients. Neurotherapy. 1996b 13:43-50.

* cited by examiner

*Primary Examiner* — Rei Tsang Shiao
(74) *Attorney, Agent, or Firm* — MCBEE MOORE & VANIK IP, LLC; Susan McBee

(57) ABSTRACT

Disclosed are methods of treating patients with AD using a rho kinase inhibitor. A preferred rho kinase inhibitor used according to the invention is fasudil, which is typically administered orally in a total daily dose of 70-140 mg. A preferred dosing regimen involves administering the daily dose in three equal portions throughout the day. Preferred methods continue for more than one month and typically at least 2 or 3 months. Some preferred methods do not treat mild cognitive impairment and patients have and MMSE score of≤23 and/or a CDR-SOB score of≥4.5.

13 Claims, No Drawings

METHODS OF USING RHO KINASE INHIBITORS TO TREAT ALZHEIMER'S DISEASE

CROSS-REFERENCE TO RELATED APPLICATIONS

This application is a continuation of United States Patent Application No. 17/996,812, filed 21 Oct. 2021, which is the National Stage entry of International Application No. PCT/US21/12588, filed 08 Jan. 2021, which claims priority to U.S. Provisional Application No. 63/014,272, filed 23 Apr. 2020, the contents of each of which are incorporated herein by reference in their entirety.

BACKGROUND

Field

Description of Related Art

Affecting nearly 50 million people worldwide, Alzheimer's disease (AD) is a chronic neurodegenerative disease that is responsible for more than 70% of the cases of dementia. About 95% of cases are sporadic, with symptoms appearing after the age of 70. Aging is the most significant risk factor associated with developing AD. Characterize by an early onset, around age 50 or younger, there is a small subset of cases that are considered to be familial, with a genetic background.

AD patients develop cognitive alterations, namely progressive episodic memory impairment, that ultimately lead to the loss of the patient's autonomy. Cognitive symptoms can include mental decline, difficulty thinking and understanding, confusion in the evening hours, delusion, disorientation, forgetfulness, making things up, mental confusion, difficulty concentrating, inability to create new memories, inability to do simple math, or inability to recognize common things. Behavioral symptoms can include aggression, agitation, difficulty with self-care, irritability, meaningless repetition of own words, personality changes, restlessness, lack of restraint, or wandering and getting lost. AD patients may also experience anger, apathy, general discontent, loneliness, mood swings, depression, hallucinations, paranoia, uncoordinated muscle movements, jumbled speech, or loss of appetite.

The two characteristic pathological findings of AD are amyloid plaques and neurofibrillary tangles (NFT). The amyloid plaques occur extracellularly, outside of the neurons, and are composed of aggregated amyloid β (Aβ) protein, which is derived from amyloid precursor protein (APP). The normal functional roles of Aβ and APP are not known, but APP may be involved in synaptic function. The NFTs found within the neurons themselves and are composed of phosphorylated aggregated Tau proteins. Tau is normally involved in stabilizing the microtubules of the axons of neurons.

It is thought, based on understanding the genes involved in familial disease, that Aβ starts the process of neurodegeneration by inducing Tau pathology, neuroinflammation and finally the neuronal loss that leads to cognitive decline.

The role of neuroinflammation in AD is unclear, likely being beneficial in early-stage disease, but evolving to a bad actor by participating in a loop of pro-inflammatory cytokine production and oxidative stress.

A central issue with interventions that target any of these processes is that of association versus causation. In order for an intervention to work in treating a disease, it must interrupt the chain of causation. While Aβ, tau and neuroinflammation are certainly associated with AD, is it not clear they are involved in causation and thus, it is unclear that affecting any of these will have any therapeutic benefit in treating the disease.

Based on the hypothesis that Aβ initiates the AD proteinopathy cascade and is the first point in the causation chain, this is the most studied clinical target. Despite the overwhelming literature showing promise in animal models, however, there have been no products that have been shown to work in AD (Ceyzériat 2020). These failures include, notably among many, Anti-Aβ42+Freud's adjuvant, Bapineuzumab, Solanezumab, Aducanumab, Verubecestat, Lanabecestat, Atabecestat, CNP520, Elenbecestat, γ-Secretase inhibitors, Bryostatin and PBT2.

Tau is a less likely target because of the evidence that it is downstream of Aβ, and thus is not causative, and so trials have been less frequent. Notably, of 15 trial targeting tau that have been initiated, already four of them have been stopped.

Neuroinflammation is the most rapidly evolving area of current clinical study, but the role of neuroinflammation in AD, and thus neuroinflammation-directed therapy, is far from clear. While epidemiological studies have suggested that treatment with nonsteroidal anti-inflammatory drugs (NSAIDs) reduce the risk of developing AD and they can decrease amyloid load in transgenic models, to date prospective studies testing anti-inflammatory drugs have shown no beneficial effect on cognition in AD. Studies targeting neuroinflammation are ongoing, but early results are not promising. Neflamapimod, a selective inhibitor of p38 mitogen-activated protein kinase showed efficacy in an animal model, but it had no effect on Aβ deposition in humans and failed its primary endpoint of improving episodic memory in Phase 2, despite reducing tau in the cerebrospinal fluid.

In view of the number of clinical failures of compounds that seemed promising in animal models of AD, a grave degree of skepticism should be applied in interpreting animal data. Even aside from the obvious issues of differences in brain complexity between rodents and humans, many of the existing models bear only a passing resemblance to the human condition. Many things can cause neural degeneration in animals and many putative drugs can halt that neural degeneration, but the underlying pathophysiology and chain of causation is unknown and it is there that a disease modifying intervention must act. It is crucial, therefore, that animal models, with their known deficiencies in the best of cases, as closely resemble the human disease as possible, in both pathology and clinical presentation.

There are a number of publications looking at the use of rho kinase inhibitors in various animal models of AD. The established models are deficient even in their basic properties. Some models involve the direct induction of neurotoxicity with agents like streptozotocin or even by direct injection of amyloid-beta into the brain. While these models may exhibit certain AD-like properties, they are merely models of neural degeneration and cannot predict treatment of AD itself. Even the transgenic models are deficient. For example, there are a number of transgenic mice that only develop amyloid plaques without NFTs, such as the APP/PS-1 mouse, perhaps the most widely reported transgenic model. There are also mice that develop tauopathies, without amyloid plaques, such as the rTG4510 tau mouse. AD is characterized by the presence of both.

Specifically, the animal models do not faithfully recapitulate human disease, partly due to species differences in neuroanatomy (Sasaguri 2017) and partly due to the deficient basic pathological bases of the models, described above. It is important also to note that the hallmark of onset in, AD, is the failure of semantic memory, which cannot be measured in any animal model and so all animal models share this deficiency as well. For example, Hamano et al., 2019, administered 12 mg/kg/day (68 mg HED) to rTG4510 tau transgenic mice and measured only tau phosphorylation/cleavage and oligomers, but no outcomes. Elliott 2018 used a triple transgenic mouse model (APP Swedish, MAPT P301L, and PSEN1 M146V) and observed reduce β-amyloid plaques in vivo at a dose of 10 mg/kg/day (intraperitoneally) fasudil (57 mg HED). Sellers 2018 used the AB42 mouse model and administered fasudil intraperitoneally at a dose of 10 mg/kg BID (226 mg HED) but monitored only β-amyloid dendritic spine loss. Couch et al. 2010 used intraventricular infusion and observed effects on dendritic branching and no outcomes relevant to wandering. Yu 2017 and Hou 2012 administered fasudil at 5 and 10 mg/kg/day intraperitoneally to APP/PS1 transgenic mice (70, 140 mg HED) and streptozotocin rats (226 mg HED), respectively and observed that latency distance and quadrant time were improved in the Morris water maze. But conflicting reports to the above also exist. For example, Turk 2018 (dissertation) used triple transgenic mice and did not observe improvements in spatial memory at 10 or 12 months of age with fasudil administered in water at 30 mg/kg and 100 mg/kg.

Some publications use unrealistic routes of administration (e.g., intraventricular injection) and many do not use appropriate dosing. In this regard, standard formulas exist for converting doses used in animals to the same dose in humans. Human equivalent dose can be calculated, for example, using Table 1 of Nair & Jacob, *J Basic Clin Pharm.* 7:27-31 (2016), which are the same conversions used by the US FDA. Becker, *Alzheimers Dis.* 15:303-325 (2008) discusses the criticality of dose in successful AD drug development and points to it as a failure point in AD drug development.

Based on currently-available but deficient animal modeling, different therapeutic strategies targeting the pathological hallmarks of AD have been tested, but have failed to show any beneficial effects in humans At present, available medications are limited to acetylcholinesterase inhibitors and N-methyl-D-aspartate (NMDA) receptor antagonists, which show only modest improvements in some symptoms. Moreover, the benefits of the approved drugs have been demonstrated only in patients with mild cognitive impairment, not in patients with established AD. There exists a significant unmet need to provide new, disease modifying therapies that show benefit in humans, not just animals.

Lastly, Kamei (1996a and 1996b) reported on using fasudil in two patients with wandering due to vascular dementia. One patient was diagnosed with Binswanger-type cerebral infarction, confirmed by MRI imaging. The other patient was diagnosed with sequelae of cerebral bleeding and multiple lacunar infarctions, confirmed by MRI. Despite the preliminary results for wandering in a few patients with subcortical vascular dementia, there is no evidence that this observation, even if confirmed by a clinical study, could be extrapolated to treatment of underlying dementias in the cortical regions of the brain like AD.

SUMMARY

The invention contemplates treating patients with AD using a rho kinase inhibitor. A preferred rho kinase inhibitor used according to the invention is fasudil, which is typically administered orally in a total daily dose of 70-140 mg. A preferred dosing regimen involves administering the daily dose in three equal portions throughout the day. Preferred methods continue for more than one month and typically at least 2 or 3 months.

The patients preferably treatable according to the invention are those with diagnosed dementia, not simply mild cognitive impairment. Preferred methods involve treating patients with a CDR score of at least 2 and/or a CDR-SOB score of at least 4.5, or even at least 6.5 and/or an MMSE score of≤23, with some preferred embodiments treating patients having an MMSE score≤20. ADAS-COG scores will usually be≥21 and sometimes are≥37. In addition to a clinical diagnosis of AD or "probable" AD, the patients treated according to the invention will generally have biomarker evidence of AD, including abnormalities in aβ and/or tau pathology as measured in the CSF and/or by PET. Other biomarker abnormalities include excessive and/or asymmetrical cortical atrophy and regional hypoperfusion. Preferred aspects of the invention exclude patients with pure vascular dementia, excluding those who meet the NINDS-AIREN criteria and/or have a Hachinski ischemia score of>7. Preferred methods to not contemplate treating patients with nimodipine.

In one embodiment of the invention, the AD patient treated with fasudil exhibits delayed progression of disease. In one embodiment, fasudil delays progression from mild to moderate cognitive decline. In another embodiment, fasudil delays progression from moderate to severe cognitive decline.

In a specific embodiment, treatment the patient treated with fasudil delays the progression from mild to moderate AD by at least 6 months, preferably, by at least one year, and more preferably, by more than one year.

In another specific embodiment, treatment the patient treated with fasudil delays the progression from moderate to severe AD by at least 6 months, preferably, by at least one year, and more preferably, by more than one year. In a specific embodiment, the progression is measured using the Clinical Dementia Rating (CDR-SOB) scale.

In a specific embodiment, the patient treated with fasudil exhibits delayed memory loss. In a specific embodiment, the delayed memory loss is assessed by improvement on the MMSE or ADAS-Cog.

In another embodiment, treatment with fasudil delays the worsening of cognitive symptoms other than memory as assessed by statistical difference in the Alzheimer's Disease Cooperative Study-Activities of Daily Living (ADCS-ADL).

In a specific embodiment, treatment with fasudil delays the progression of driving impairment.

In yet another embodiment, fasudil reduces the rate of emergence of undesired behavior in patients with AD who were asymptomatic at baseline, including, for example, aggression, agitation, difficulty with self-care, irritability, meaningless repetition of own words, personality changes, restlessness, lack of restraint, or wandering and getting lost.

In another embodiment, fasudil treatment reduces the occurrence of gait apraxia or balance deficits.

In another specific embodiment, treatment with fasudil eliminates or delays the need for institutionalization of an AD patient. In a specific embodiment, the patient exhibits agitation.

In one embodiment of the invention, the patient treated wherein the treatment eliminates use of chemical restraints including antipsychotic medications (e.g., aripiprazole, clozapine, haloperidol, olanzapine, quetiapine, risperidone and ziprasidone) to combat behavioral symptoms.

In another embodiment, the patient treated with fasudil is also treated with an anti-depressant such as trazodone, and SSRIs such as citalopram or escitalopram, paroxetine, fluoxetine, or sertraline. In a further embodiment, treatment with fasudil reduces the advancement of neurodegeneration from the entorhinal cortex and hippocampus to the frontal cerebral cortex.

In In another embodiment, the patient treated has limbic-predominant associated AD disease. In a further embodiment, the limbic-predominant patient is a female.

In another embodiment, the AD patient treated with fasudil has neurodegeneration primarily in the hippocampal region of the brain. In another embodiment, the patient to be treated has neurodegeneration primarily in the cortical region of the brain and not the hippocampal region. In a specific embodiment, the hippocampal-spared patient is male. In a further specific embodiment, the hippocampal-spared AD male patient treated has early-onset AD.

In a further embodiment, the patient treated with fasudil has posterior cortical atrophy (PCA).

In a specific embodiment, the patient is male. In another specific embodiment, the patient has early-onset dementia. In a specific embodiment, the patient has a defect in a presenilin-1 gene, an amyloid precursor protein (APP) gene, and/or a presenilin gene. In a further embodiment, the patient treated has a defect in, or differential expression of an ApoE ε4 allele.

In another embodiment, the patient treated with fasudil exhibits deficits in at least one of memory, executive functioning, language, and visuospatial functioning.

In another embodiment, the patient treated with fasudil exhibits deficits in all of memory, executive functioning, language, and visuospatial functioning.

In a further embodiment, the patient treated with fasudil exhibits a greater deficit in memory, as compared to executive functioning, language, and visuospatial functioning. In a specific embodiment, such patient has a defect in, or differential expression of an ApoE ε4 allele. In another embodiment, the memory deficit is in episodic memory.

In a further embodiment, the patient treated with fasudil exhibits a greater deficit in language, as compared to executive functioning, memory, and visuospatial functioning.

In a further embodiment, the patient treated with fasudil exhibits a greater deficit in executive functioning, as compared to memory, language, and visuospatial functioning.

In a further embodiment, the patient treated with fasudil exhibits a greater deficit in visuospatial functioning, as compared to executive functioning, language, and memory.

DETAILED DESCRIPTION OF A PREFERRED EMBODIMENT

AD is a neurodegenerative disease that presents as an insidious progressive impairment of semantic memory. In the early stages, when memory impairment is the main presenting feature, personality and social skills often appear preserved. As AD progresses, other aspects of cognition and behavior become impaired with the appearance of aphasia and apraxia. Language impairment can include, in the early stages, difficulty in naming and word-finding, with progressive impairment of verbal and written comprehension and expression. Visuospatial abilities, analytic and synthetic abilities, judgment, and insight are all progressively affected and patients may experience delusions and hallucinations. Behavioral changes appearing may include restlessness, irritability, agitation, verbal or physical aggression, wandering, pacing and disinhibition. In the final stages, cognitive functions entirely deteriorate and patient may exhibit marked limb rigidity, resulting in loss of mobility, culminating in incontinence of urine and feces with death typically resulting from infections that often cause pneumonia.

ROCK Inhibitors

The inventive methods contemplate the administration of a rho kinase (ROCK) inhibitor in the treatment of a disease or condition. Two mammalian ROCK homologs are known, ROCK1 (aka ROKβ, Rho-kinase β, or p160ROCK) and ROCK2 (aka ROKα) (Nakagawa 1996). In humans, the genes for both ROCK1 and ROCK2 are located on chromosome 18. The two ROCK isoforms share 64% identity in their primary amino acid sequence, whereas the homology in the kinase domain is even higher (92%) (Jacobs 2006; Yamaguchi 2006). Both ROCK isoforms are serine/threonine kinases and have a similar structure.

A large number of pharmacological ROCK inhibitors are known (Feng, LoGrasso, Defert, & Li, 2015). Isoquinoline derivatives are a preferred class of ROCK inhibitors. The isoquinoline derivative fasudil was the first small molecule ROCK inhibitor developed by Asahi Chemical Industry (Tokyo, Japan). The characteristic chemical structure of fasudil consists of an isoquinoline ring, connected via a sulphonyl group to a homopiperazine ring. Fasudil is a potent inhibitor of both ROCK isoforms. In vivo, fasudil is subjected to hepatic metabolism to its active metabolite hydroxyfasudil (aka, M3). Other examples of isoquinoline derived ROCK inhibitors include dimethylfasudil and ripasudil.

Other preferred ROCK inhibitors are based on based on 4-aminopyridine structures. These were first developed by Yoshitomi Pharmaceutical (Uehata et al., 1997) and are exemplified by Y-27632. Still other preferred ROCK inhibitors include indazole, pyrimidine, pyrrolopyridine, pyrazole, benzimidazole, benzothiazole, benzathiophene, benzamide, aminofurazane, quinazoline, and boron derivatives (Feng et al., 2015). Some exemplary ROCK inhibitors are shown below:

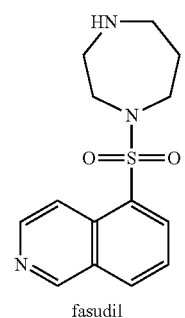

fasudil a

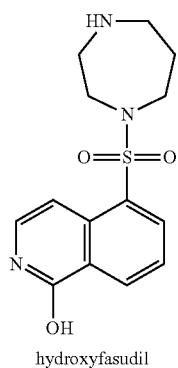

hydroxyfasudil

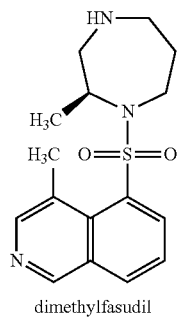

dimethylfasudil

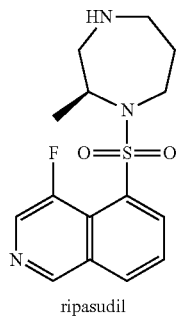

ripasudil

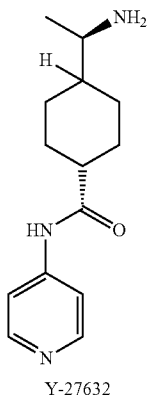

Y-27632

ROCK inhibitors according to the invention may have more selective activity for either ROCK1 or ROCK2 and will usually have varying levels of activity on PKA, PKG, PKC, and MLCK. Some ROCK inhibitors may be highly specific for ROCK1 and/or ROCK2 and have much lower activity against PKA, PKG, PKC, and MLCK.

A particularly preferred ROCK inhibitor is fasudil. Fasudil may be exist as a free base or salt and may be in the form of a hydrate, such as a hemihydrate. As used herein, unless specifically noted, the name of any active moiety, such as fasudil, should be considered to include all forms of the active moiety, including the free acid or base, salts, hydrates, polymorphs and prodrugs of the active moiety.

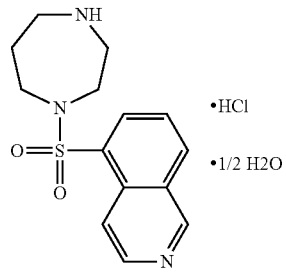 [SMILES: O=S(=O)(c1cccc2cnccc12)N1CCCNCC1 ; "·1/2 H2O" ; Cl]

Hexahydro-1-(5-Isoquinolinesulfonyl)-1H-1,4-Diazepine Monohydrochloride Hemihydrate Fasudil is a selective inhibitor of protein kinases, such as ROCK, PKC and MLCK and treatment results in a potent relaxation of vascular smooth muscle, resulting in enhanced blood flow (Shibuya 2001). A particularly important mediator of vasospasm, ROCK induces vasoconstriction by phosphorylating the myosin-binding subunit of myosin light chain (MLC) phosphatase, thus decreasing MLC phosphatase activity and enhancing vascular smooth muscle contraction. Moreover, there is evidence that fasudil increases endothelial nitric oxide synthase (eNOS) expression by stabilizing eNOS mRNA, which contributes to an increase in the level of the potent vasodilator nitric oxide (NO), thereby enhancing vasodilation (Chen 2013).

Fasudil has a short half-life of about 25 minutes, but it is substantially converted in vivo to its 1-hydroxy (M3) metabolite. M3 has similar effects to its fasudil parent molecule, with slightly enhanced activity and a half-life of about 8 hours (Shibuya 2001). Thus, M3 is likely responsible for the bulk of the in vivo pharmacological activity of the molecule. M3 exists as two tautomers, depicted below:

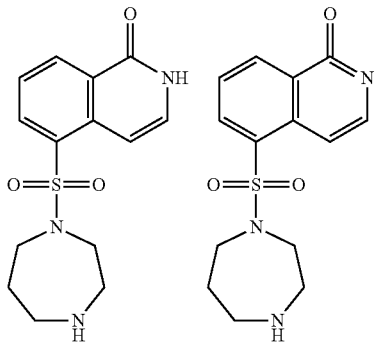

The ROCK inhibitors used in the invention, such as fasudil, include pharmaceutically acceptable salts and hydrates. Salts that may be formed via reaction with inorganic and organic acid. Those inorganic and organic acids are included as following: hydrochloric acid, hydrobromide acid, hydriodic acid, sulphuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid.

Pharmaceutical Compositions

Pharmaceutical compositions of ROCK inhibitors usable in the are generally oral and may be in the form of tablets or capsules and may be immediate-release formulations (ie, those in which no elements of the formulation are designed to substantially control or retard the release of the ROCK inhibitor upon administration) or may be controlled- or extended-release formulations, which may contain pharmaceutically acceptable excipients, such as corn starch, mannitol, povidone, magnesium stearate, talc, cellulose, methylcellulose, carboxymethylcellulose and similar substances. A pharmaceutical composition comprising a ROCK inhibitor and/or a salt thereof may comprise one or more pharmaceutically acceptable excipients, which are known in the art. Formulations include oral films, orally disintegrating tablets, effervescent tablets and granules or beads that can be sprinkled on food or mixed with liquid as a slurry or poured directly into the mouth to be washed down.

Pharmaceutical compositions containing ROCK inhibitors, salts and hydrates thereof can be prepared by any method known in the art of pharmaceutics. In general, such preparatory methods include the steps of bringing a ROCK inhibitor or a pharmaceutically acceptable salt thereof into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition used in accordance with the methods of the present invention may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the pharmaceutical composition used in the methods of the present invention may comprise a diluent. Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

In certain embodiments, the pharmaceutical composition used in the methods of the present invention may comprise a granulating and/or dispersing agent. Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

In certain embodiments, the pharmaceutical composition used in the methods of the present invention may comprise a binding agent. Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM.®.), and larch arabogalactan), alginates, polyethylene oxide, polyethylene glycol, inorganic calcium salts, silicic acid, polymethacrylates, waxes, water, alcohol, and/or mixtures thereof.

In certain embodiments, the pharmaceutical composition used in the methods of the present invention may comprise a preservative. Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

In certain embodiments, the pharmaceutical composition used in the methods of the present invention may comprise an antioxidant. Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

In certain embodiments, the pharmaceutical composition used in the methods of the present invention may comprise a chelating agent. Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the pharmaceutical composition may comprise a buffering agent together with the ROCK inhibitor or the salt thereof. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

In certain embodiments, the pharmaceutical composition used in the methods of the present invention may comprise a lubricating agent. Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

In other embodiments, the pharmaceutical composition of containing a ROCK inhibitor or salt thereof will be administered as a liquid dosage form. Liquid dosage forms for oral and parenteral administration include pharmaceutically acceptable emulsions, microemulsions, solutions, suspensions, syrups, and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Some compositions of the invention relate to extended- or controlled-release formulations. These may be, for example, diffusion-controlled products, dissolution-controlled products, erosion products, osmotic pump systems or ionic resin systems. Diffusion-controlled products comprise a water-insoluble polymer which controls the flow of water and the subsequent egress of dissolved drug from the dosage from. Dissolution-controlled products control the rate of dissolution of the drug by using a polymer that slowly solubilizes or by microencapsulation of the drug—using varying thicknesses to control release. Erosion products control release of drug by the erosion rate of a carrier matrix. Osmotic pump systems release a drug based on the constant inflow of water across a semi permeable membrane into a reservoir which contains an osmotic agent. Ion exchange resins can be used to bind drugs such that, when ingested, the release of drug is determined by the ionic environment within the gastrointestinal tract.

Treatable Patients

The invention contemplates using rho kinases in the treatment of patients with AD. The contemplated therapy is believed to be disease-modifying and so the inventive methods specifically contemplate treating or alleviating the various clinical presentations and symptoms of the disease, along with improvements in markers of AD.

The AD patient treatable according to the invention may show one or more of the following deficits and the invention contemplates methods of improving each of these deficits. Deficits may include: impairment of semantic memory (with or without personality and/or social skills preserved); aphasia; apraxia; difficulty in naming; difficulty in word-finding; impairment of verbal comprehension; impairment of written comprehension; impairment of written expression; impairment of visuospatial abilities, impairment of analytic abilities; impairment of synthetic abilities; impairment of judgment; impairment of insight; delusions; hallucinations; restlessness; irritability; agitation; verbal aggression; physical aggression; wandering; pacing; and disinhibition.

The American Psychiatric Association differentiates between mild and major neurocognitive impairment:
  Mild neurocognitive impairment is defined as a cognitive decline one to two standard deviations from normal on formal cognitive testing that does not interfere with independence and is not due to delirium or other medical or psychiatric disorder.
  Major neurocognitive impairment is defined as a cognitive decline two standard deviations or more from normal on formal cognitive testing that does interferes with independence and is not due to delirium or other medical or psychiatric disorder.

Patients treatable according to the invention typically will have a major neurocognitive impairment according to these criteria, such that the impairment interferes with their independence. Impairment of independence can be assessed using a scale that measures activities of daily living (ADL), including scales like the Barthel Index. Often, patients treatable according to the invention will have restricted independence in that they are residents in an assisted living or a memory care facility and are not community- or home-dwelling due to their condition.

Diagnostic and Statistical Manual of Mental Disorders Fifth Edition (DSM-V) provides a useful framework for the identification of patients treatable according to the invention. The DSM-V provides definitions of dementia syndrome and probable Alzheimer disease dementia.

Dementia syndrome requires objective cognitive or behavioral impairment in at least two of the following: memory; reasoning and handling complex tasks; visuospatial abilities; language functions; and personality, behavior, or comportment. It also requires a decline from previous level of functioning and a functional impairment.

Probable Alzheimer disease dementia requires: the criteria for dementia syndrome are met; an insidious onset; gradual progression; amnestic or non-amnestic (language or executive) initial symptoms; and no other neurologic, psychiatric, or general medical disorders of severity that can interfere with cognition. The DSM-V indicates that diagnostic certainty can be increased with positive biomarkers (e.g., CSF Aβ/tau, amyloid positron emission tomography, and hippocampal atrophy on MRI). In accordance with the DSM-V, the invention particularly contemplates treating patients with probable Alzheimer dementia where the patients are also shown to be positive on one or more AD biomarkers.

A working group convened by the National Institute on Aging (NIA) and the Alzheimer's Association sets forth widely accepted diagnostic criteria for AD dementia (McKhann 2011). The NIA criteria first set for a diagnostic framework for diagnosing dementia (the appearance of cognitive or behavioral symptoms that adversely affect the functional capacity of the patient), irrespective of cause. Probable AD dementia is diagnosed by the evolution of the symptoms and the presentation of certain cognitive deficits, most commonly amnestic (impaired learning and recall of recent information), but also various non-amnestic deficits, like word-finding, spatial cognition, and executive dysfunction. Probable AD also requires an exclusion of VaD, dementia with Lewy Bodies (DLB), behavioral variant of frontotemporal dementia (bvFTD), semantic variant primary progressive aphasia or nonfluent/agrammatic variant primary progressive aphasia, and other causes like another active neurological disease, or a non-neurological medical comorbidity or use of medication that could adversely affect cognition. Probable AD dementia is diagnosed with greater certainty when one or more biomarkers of AD pathology are shown to be present.

As part of the NIA or DSM-V diagnosis or independent of them, diagnosis of AD patients treated according to the invention can be facilitated using imaging and measuring biomarkers in cerebrospinal fluid (CSF). The most widely used CSF biomarkers for Alzheimer's disease measure certain proteins: beta-amyloid 42 (the major component of amyloid plaques in the brain), tau, and phospho-tau (major components of tau tangles in the brain). In Alzheimer's disease, beta-amyloid 42 levels in CSF are low, and tau and phospho-tau levels are high, compared with levels in people without Alzheimer's or other causes of dementia.

Imaging is as useful tool in diagnosing dementia, in particular computerized tomography (CT), magnetic resonance imaging (MRI) and positron emission spectroscopy (PET). Neural degeneration results in brain atrophy and this can be detected and quantified. Patients treatable according to the invention may show global brain atrophy, measurable on the global cortical atrophy (GCA) scale. A score of 1 on the scale may be considered normal in an elderly patient, but scores of 2 or 3 should generally be considered to be abnormal. Subjects with a GCA score of 2 or 3 are preferably treatable according to the invention. Severe cases of atrophy may show pronounced ventricular enlargement and such patients are suitably treated using the inventive methods. Asymmetric and/or regional atrophy detected by MRI, particularly of the temporal and/or parietal regions, is highly suggestive of AD. Automated tools are increasingly available that can perform these functions in order to detect abnormal brain atrophy indicative of AD.

Fluorodeoxyglucose (FDG) PET scans measure glucose use in the brain. Glucose, a type of sugar, is the primary source of energy for cells. Studies show that people with dementia often have abnormal patterns of decreased glucose use in specific areas of the brain. An FDG PET scan can show a pattern that may support a diagnosis of a specific cause of dementia. The invention contemplates treating patients with evidence of AD pathology detected by PET, including but not limited to FDG PET. FDG PET detects regions of glucose hypometabolism, indicating metabolic impairment. AD patients treatable according to the invention often show temporal and parietal hypometabolism.

Amyloid PET scans measure abnormal deposits of a protein called beta-amyloid. Higher levels of beta-amyloid are consistent with the presence of amyloid plaques, a hallmark of Alzheimer's disease. Several tracers may be used for amyloid PET scans, including florbetapir, flutemetamol, florbetaben, and Pittsburgh compound B. The invention contemplates treating patients with evidence of amyloid deposits by PET scan using on or more of the foregoing tracers.

Tau PET scans detect abnormal accumulation of a protein, tau, which forms tangles in nerve cells in Alzheimer's disease and many other dementias. Several tau tracers, such as AV-1451, PI-2620, and MK-6240, are being studied in clinical trials and other research settings. The invention contemplates treating patients with evidence of NFTs by PET scan using on or more of the foregoing tracers.

Regional hypoperfusion is also associated with functional deficits seen in AD. Hypoperfusion may be detected by a number of methodologies, including spin-labeling MRI and single-photon emission computed tomography (SPECT). The invention contemplates treating patients with evidence of regional hypoperfusion, detected by spin-labeling MRI, SPECT and other methods known to the skilled artisan.

In one aspect, the invention excludes patients with vascular dementia (VaD). While some patients may have mixed pathology, true VaD, which is dementia precipitated by a cardiovascular event, such as an ischemic or hemorrhagic stroke, or a chronic cardiovascular condition, such as Binswanger's disease or lucunar dementia. Excluded patients can be readily identified using the criteria of the National Institute of Neurological Disorders and Stroke (NINDS) and the Association Internationale pour 1 a Recherche et 1' Enseignement en Neurosciences (AIREN) (the NINDS-AIREN criteria) (Wetterling 1996; Román 1993). Thus, patients identified according to the NINDS-AIREN criteria are excluded. Another useful tool in excluding VaD patients is the Hachinski Ischemia Score, in which diagnosed stroke, rapid onset, fluctuating course, and focal signs and symptoms, all indicative of stroke, are more heavily weighted. According to Hachinski, the following features of patients with dementia are scored with two points: abrupt onset; fluctuating course; history of strokes; focal neurological symptoms; focal neurological signs. The following elements that are less likely to be related to a cardiovascular event (and thus VaD) are scored with one point each: emotional incontinence; stepwise deterioration; history of hypertension; nocturnal confusion; evidence of associated atherosclerosis; relative preservation of personality; depression; and somatic complaints. Typically, a score>7 would indicate the patient has VaD. Hence, patients treated in accordance with the invention will typically have an Hachinski score of≤7 and patients with a Hachinski score of>7 would be excluded.

Patients treatable according to the invention will typically score poorly on cognitive scales, such as the mini mental state exam (MMSE). A threshold of≤23 on the MMSE is set for dementia, with score of≤15 Representing severe dementia. Patients with an MMSE score of 24-27 may have "pre-"AD or "prodromal" AD, but they do not yet have AD and are not generally treated according to the invention. Patients treated according to the invention preferably have an MMSE score of less than 23 and some patients have a minimum MMSE of 15. In certain aspects of the invention treated patients will have an MMSE score of≤20 or≤18 or≤16. Once the MMSE falls below 15, the Severe Impairment Battery (SIB) is a useful assessment too.

Other short tools for assessing dementia/diminished cognition and for measuring cognitive improvement include: the Eight-item Informant Interview to Differentiate Aging and Dementia (AD8); the Annual Wellness Visit (AWV); the General Practitioner Assessment of Cognition (GPCOG); Health Risk Assessment (HRA); Memory Impairment Screen (MIS); the Montreal Cognitive Assessment (MoCA); the St. Louis University Mental Status Exam (SLUMS); and the Short Informant Questionnaire on Cognitive Decline in the Elderly (Short IQCODE).

Other cognitive or functional measures designed for Alzheimer's disease, include the Clinical Dementia Rating (CDR), the Alzheimer's Disease Assessment Scale-Cognitive Subscale (ADAS-Cog) and the Alzheimer's Disease Cooperative Study-Clinical Global Impression of Change (ADCS-CGIC), including variants thereof.

Another useful scale for measuring some of the symptoms of dementia in AD is the Cohen-Mansfield Agitation Inventory (CMAI).

The CDR Dementia Staging Instrument is a 5-point scale used to characterize six domains of cognitive and functional performance in AD: Memory, Orientation, Judgment & Problem Solving, Community Affairs, Home & Hobbies, and Personal Care. It is scored according to the following scale: 0=Normal; 0.5=Very Mild Dementia; 1=Mild Dementia; 2=Moderate Dementia; 3=Severe Dementia. Patients treatable according to the invention will preferably have a CDR score of 2 or 3. The CDR is generally scored according to an algorithm the differentially weighs the sub-scores (0, 0.5, 1, 2 or 3) from the various domains. The CDR may be scored in an alternative manner which simply adds up the sub-scores for each domain. The so-called sum-of-boxes (SOB) method is equally valid, but has higher resolution, yielding scores from 0 (normal) to 18 (score of 3 on every domain). Patients treatable according to the invention will generally score a minimum of 4.5 using the CDR-SOB scoring.

Dosing Regimens

The treatment methods of the present invention, while contemplating various routes of administration, are particularly suited to oral administration. In accordance with the treatment methods of the present invention, an effective amount of a ROCK inhibitor or a pharmaceutically acceptable salt thereof for administration one or more times a day may comprise from about 10 mg to about 1000 mg. The methods of the invention are preferably accomplished using fasudil administered orally in a total daily dose of between 70 mg and 140 mg. Fasudil hydrochloride hemihydrate, for example, is suitably administered in a daily amount of about 10 mg to about 500 mg, about 10 mg to about 400 mg, about 10 mg to about 200 mg, about 10 mg to about 100 mg, about 20 mg to about 10 mg. One preferred dosing regimen involves the treatment with 25, 30 or 40 mg of fasudil hydrochloride hemihydrate three times per day using an immediate-release formulation, for a total daily dose of 75-120 mg. Most preferred dosing exceeds a daily dose of 60 mg, with most preferred ranges for daily dosing being 70 mg to 120 mg administered in three equal amounts during the day. Other preferred daily doses will range from 90 mg to 120 mg per day or 80 mg to 140 mg per day. A further dosing regimen involves the treatment with, 35 to 60 mg of fasudil hydrochloride hemihydrate only two times per day using an immediate-release formulation, for a total daily dose of 70-120 mg. Based on ROCK inhibitory activity, one skilled in the art can readily extrapolate the provided dosing ranges for fasudil to other ROCK inhibitors. A preferred embodiment is 45 mg of fasudil hydrochloride hemihydrate two times per day using an immediate-release formulation.

Certain patient sub-populations, such as renally impaired patients and/or older patients (e.g., 65 or older) may need lower doses or extended release formulations instead of immediate release formulations. Fasudil hydrochloride hemihydrate may have higher steady-state concentrations when given at usual doses to patients with renal disease and lower doses to lower the Cmax or delay the time to Cmax (increase the Tmax) may be required.

Renal dysfunction occurs with age and as the result of numerous disorders, including liver cirrhosis, chronic kidney disease, acute kidney injury (for example, due to administering a contrast agent), diabetes (Type 1 or Type 2), autoimmune diseases (such as lupus and IgA nephropathy), genetic diseases (such as polycystic kidney disease), nephrotic syndrome, urinary tract problems (from conditions such as enlarged prostate, kidney stones and some cancers), heart attack, illegal drug use and drug abuse, ischemic kidney conditions, urinary tract problems, high blood pressure, glomerulonephritis, interstitial nephritis, vesicoureteral, pyelonephritis, sepsis. Kidney dysfunction may occur in other diseases and syndromes, including non-kidney-related diseases that may occur along with kidney dysfunction, for example pulmonary artery hypertension, heart failure, and cardiomyopathies, among others.

Kidney function is most often assessed using serum (and/or urine) creatinine. Creatinine is a breakdown product of creatine phosphate in muscle cells and it is produced at a constant rate. It is excreted by the kidneys unchanged, principally through glomerular filtration. Accordingly, elevated serum creatinine is a marker for kidney dysfunction and it is used to estimate glomerular filtration rate.

Normal levels of creatinine in the blood are approximately 0.6 to 1.2 mg/dL in adult males and 0.5 to 1.1 mg/dL in adult females. When creatinine levels exceed these figures, the subject has renal dysfunction, and is, therefore, treatable according to the invention. Mild renal impairment/dysfunction occurs in the range of 1.2 mg/dL to 1.5 mg/dL. Moderate renal impairment/dysfunction is considered to occur at creatinine levels exceeding 1.5 mg/dL. Severe renal impairment, which includes what is considered to be renal failure, is defined as a serum creatinine level of≥2.0 mg/dL or the use of renal replacement therapy (such as dialysis). Treating subjects with mild, moderate and severe renal impairment is specifically contemplated.

As indicated, creatinine levels are considered to be a surrogate for glomerular filtration rate and serum creatinine levels alone may be used to estimate glomerular filtration rate using the Cockroft-Gault equation.

Generally, creatinine clearance of less than 60 mL/min (corresponding roughly to creatinine of>1.2 mg/dL) is considered moderate renal dysfunction. A glomerular filtration rate below 40 mL/min (corresponding approximately to creatinine levels exceeding 1.5 mg/dL) or especially 30 mL/min is considered severe renal dysfunction.

In general, creatinine clearance (estimated glomerular filtration rate) may be derived directly from serum creatinine using the Cockroft—Gault equation:

creatinine clearance=(((140−age in years)×(wt in kg))×1.23)/(serum creatinine in µmol/L)

For women the result of the calculation is multiplied by 0.85.

Empirically measured creatinine clearance may also be used directly as an estimate of glomerular filtration rate by looking at serum creatinine and urine creatinine levels. Specifically, urine is collected over 24 hours and the following equation is applied to ascertain creatinine clearance:

Creatinine Clearance (mL/min)=Urine Creatinine Concentration (mg/mL)*24 hour urine volume (mL)/Plasma Creatinine Concentration (mg/mL) *24 hour*60 minutes In one embodiment, dose of fasudil for mild to moderate renal impairment is reduced to 50-80 mg per day. In another embodiment, the dose of fasudil is not reduced but is administered one time per day in an extended release dosage form.

In another embodiment, the dose is not reduced for mild to moderate renal impairment.

In one embodiment, the dose of fasudil is reduced to 30-45 for severe renal impairment. In another embodiment, the dose of fasudil is not reduced but is instead administered one time per day in an extended release dosage form.

In a further embodiment, the dose is reduced where serum creatinine (SCr)>2 and/or an increase in SCr>1.5×from baseline, and/or a decrease in eGFR>25% from baseline.

Patient size is an important factor to consider when using creatinine-based estimates of renal function. The units of drug clearance are volume/time (mL/min), whereas the units of estimated GFR for chronic renal disease are volume/time/standard size (mL/min/1.73m$^2$). Generally, doses may be adjusted down (e.g., 40-50 mg per day) for smaller patients and up for larger (e.g., 120 mg per day) for obese patients. A smaller male would be about 160 pounds or less. A smaller female patient would weigh about 130 pounds or less. Patients having a Body Mass Index of 30 and higher is considered obese.

In addition, older patients may need a lower dose at initiation, with a gradual increase to the recommended dose after days or weeks. In another embodiment, older patients may need lower doses for the duration of treatment. The aged population includes the "young old" who are 65-74, the "old old" who are 75-84 and the "frail elderly" who are 85 and older. For example, a starting dose of 30 mg per day for two weeks, followed by 60 mg per day for 4 weeks, then by 90 mg per day. Titration may even be warranted up to about 120 mg per day.

Another embodiment involves the treatment with 60-120 mg of fasudil hydrochloride hemihydrate once per day in an extended release dosage form. Treatment with an extended release total daily dose of 90 mg fasudil hydrochloride hemihydrate once per day is preferred. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment. Most preferred methods contemplate that treatment begins after the onset or appearance of symptoms.

The methods of the invention also contemplate administering ROCK inhibitors with other compounds used to treat dementia or other symptoms of dementia. They may be administered in combination, a single dosage form, in a common dosing regimen or administered to the same patient at different times of the day using different dosing regiments.

Two classes of drugs are used to treat dementia and have been shown to improve cognition: acetylcholinesterase inhibitors and N-methyl-D-aspartate (NMDA) receptor antagonists. Generally used in the early stages of disease, acetylcholinesterase inhibitors prevent the breakdown of the neurotransmitter acetylcholine. These drugs include piperidines like donepezil (Aricept), phenanthrene derivatives, like galantamine (Razadyne), and carbamates like rivastigmine (Exelon). NMDA receptor antagonists include the uncompetetitive inhibitor memantine (Namenda). A combination of memantine and donepezil (Namzaric) is also available.

In some embodiments, the patients are administered fasudil in combination with other actives approved to treat dementia, including but not limited to cholinesterase inhibitors and NMDA receptor antagonists. In one embodiment, the cholinesterase inhibitor is selected from the group consisting of donepezil, rivastigmine, and galantamine Exemplary doses of the cholinesterase inhibitors include 3-25 mg per day, more preferably 6-12 mg per day. In another embodiment, the NMDA receptor antagonist is memantine. In a specific embodiment, memantine is administered at a dose of 5-28 mg per day, preferably 15-20 mg per day. In a further embodiment, the co-administered active is a combination of donepezil and memantine at a dose of 28 mg memantine and 10 mg donepezil.

In a specific embodiment, the combination of fasudil with cholinesterase inhibitors is administered to AD patients. In a further embodiment, the combination of fasudil with cholinesterase inhibitors is administered to patients with mixed dementia that is predominantly of the AD type. In yet a further embodiment, the combination of fasudil with cholinesterase inhibitors is not administered to patients only vascular dementia.

Dextromethorphan hydrobromide is another an uncompetitive NMDA receptor antagonist that also has activity as a sigma-1 receptor agonist. Marketed in combination quinidine sulfate (a CYP450 2D6 inhibitor), the product Nudexta is indicated for the treatment of pseudobulbar affect, which occurs in many forms of dementia. In one embodiment, a patient is treated with product useful in treating pseudobulbar affect, like Nudexta, and fasudil.

In a further embodiment, the patient treated with fasudil is also being treated with active agents including mood stabilizers, benzodiazepines, antipsychotics, anti-agitation drugs, or sleep aids. In a specific embodiment, the patient treated with fasudil is not being treated with risperidone, aripiprazole, quetiapine, carbamazepine, gabapentin, prazocin, trazodone or lorazepam.

In a further embodiment the patient treated with fasudil is being treated for depression. In a specific embodiment, the patient is treated with an anti-depressant such as citalopram or escitalopram.

In another embodiment, fasudil is administered in combination with an antioxidant such as alpha tocopherol. In a specific embodiment, the alpha tocopherol is administered in a dose of 1000-2000 IU per day.

In a further embodiment, fasudil is administered width an NSAID. In a specific embodiment, the NSAID is ibuprofen, naproxen, diclofenac, or indomethacin is administered with fasudil.

The methods of the invention in certain embodiments, especially those contemplating parenteral dosing, do not include the administration of a statin (rosuvastatin, especially) to a patient also receiving a rho kinase inhibitor. The methods of the invention in certain embodiments, especially those contemplating parenteral dosing, do not include the administration of nimodipine to a patient also receiving a rho kinase inhibitor.

Results of the Methods

The methods of the invention are considered to be disease modifying, such that they will result in improvements in all related signs and symptoms. Such improvements may be absolute, in that a treated patient will actually show an improvement over time relative to a previous measurement. Improvements are more typically measured relative to control patients. Control patients may be historical and/or based on the known natural history of similarly-situated patients, or they may be controls in the sense that they receive placebo or simply standard of care in these same clinical trial. Comparison to controls is especially instructive as it is unlikely that the course of the disease will be fully reversed and so results are measure in terms of decreased deterioration relative to controls/expectations.

Improvements can be assessed using one or more of the following scales: the MMSE; the SIB; the ADB; the AWV; the GPCOG; the HRA; the MIS; the MoCA; the SLUMS; the Short IQCODE; the CDR; the ADAS-Cog; the ADCS-CGIC; and the CMAI, including variants thereof.

Improvements resulting from the inventive methods will generally be at least 10%; 15%; 20%; 25%; 30%; 35%; 40%; 45% or 50%, absolute or in comparison to a control. In another embodiment, improvements resulting from the inventive methods will be at least 50% or more, absolute or in comparison to a control. In preferred embodiments, improvements resulting from the inventive methods will be at least 75%, absolute or relative to a control. In a specific embodiment, the improvement is relative to the same patient prior to treatment with fasudil.

Treatment using the inventive methods generally result in improved cognitive functioning. Patients will generally show improvement on the MMSE and/or the SIB of at least 3 points during the early stages of treatment and declines in cognition are slowed relative to control patients, generally maintaining at least a 1- or 2-point differential in treated and control patients.

A typical patient treated according to the invention may show improvements of at least 0.5 points on the CDR-SOB, but in any event will show a reduced rate of decline, manifesting as at least a 1-point differential on the CDR-SOB versus untreated controls after treatment for at least 6 months.

Patient treated according to the invention are also expected to show improvements in one or more of the following: semantic memory (with or without personality and/or social skills preserved); aphasia; apraxia; naming; word-finding; verbal comprehension; written comprehension; written expression; visuospatial abilities, analytic abilities; synthetic abilities; judgment; insight; delusions; hallucinations; restlessness; irritability; agitation; verbal aggression; physical aggression; wandering; pacing; and disinhibition.

EXAMPLE

Eighty patients diagnosed with probable AD with at least one positive AD biomarker (aβand/or tau abnormality) are recruited. Patients with VaD, DLB, bvFTD, or semantic variant primary progressive aphasia or nonfluent/agrammatic variant primary progressive aphasia are excluded, along with patients with another concurrent active neurological disease. Patients with a non-neurological comorbidity or who use medication that could adversely affect cognition are also excluded. Patients have a maximum MMSE score of 23 and a minimum MMSE score of 15.

Cohorts of 20 patients are treated orally with fasudil or placebo in a dose escalating manner Each group is randomized 10 patients each to placebo or drug and treated for 60 days. At the end of 30 days, based on assessment of adverse event, the next cohort with a higher dose is begun. At the end of 60 days, patients will be assessed for efficacy and safety and will be re-randomized into the next higher dose in the absence of dose-limiting side effects. Oral dosing using 10 mg immediate release tablets starts with the first cohort at 60 mg per day (administered in 3 equal doses throughout the day), the second cohort at 90 mg per day (administered in 3 equal doses throughout the day), the third cohort at 120 mg per day (administered in 3 equal doses throughout the day) and the third cohort at the maximum planned dose is 150 mg per day (administered in 3 equal doses throughout the day).

No effect in cognition is observed with the 60 mg dose at 60 days, whereas each of the other doses show improvements at 60 days versus control. When the first cohort is escalated to 90 mg per day, a difference in cognition between treated and control in that cohort is observed. Cognition improves in a dose-dependent manner across all doses. A dose-dependent increase in creatinine, indicating possible kidney dysfunction are seen. Only 50% of the subjects who are escalated to the 120 mg per day dose are also escalated to the 150 mg dose and 25% of patients treated with 150 mg daily are dose-reduced due to elevated creatinine levels.

It is determined that the optimal dose for improving cognition in AD dementia is between 90 mg and 120 mg per day. Below 90 mg, there is no efficacy and above 120 mg elevated creatinine 20 becomes dose-limiting in many patients.

List of References

Becker RE, Greig NH, Giacobini H, Why do so many drugs for Alzheimer's disease fail in development? Time for new methods and new practices? *Alzheimers Dis.* 15:303-325 (2008).

Ceyzériat et al., Learning from the Past: A Review of Clinical Trials Targeting Amyloid, Tau and Neuroinflammation in Alzheimer's Disease. *Current Alzheimer Research.* 2020; 17: 1-13.

Chen M, Liu A, Ouyang Y, Huang Y, Chao X, Pi R. 2013. Fasudil and its analogs: a new powerful weapon in the long war against central nervous system disorders? Expert Opin Investig Drugs. 22:537-50.

Couch BA, DeMarco GJ, Gourley SL, Koleske AJ, Increased Dendrite Branching in Aβ/PS1 Mice and Elongation of Dendrite Arbors by Fasudil Administration. Alzheimers Dis. 2010; 20(4): 1003-1008.

Elliott C, Rojo A, Ribe E, Broastock M, Xia W, Morin P, Semenov M, Baillie G, Cuadrado A, Al-Shawi R, Ballard C, Simons P, Killick R, A role for APP in Wnt signalling links synapse loss with β-amyloid production. Translational Psychiatry. 2018; 8(179).

Feng Y, LoGrasso P, Defert O, Li R, Rho Kinase (ROCK) Inhibitors and Their Therapeutic Potential. J Med Chem. 2016; 59(6): 2269-2300.

Folstein MF, Folstein SE, McHugh PR. "Mini-mental state": a practical method for grading the cognitive state of patients for the clinician. J Psychiatr Res. 1975;12:189-198.

Hamano T, Shirafuji N; Yen S; Yoshida H, Kanaan N, Hayashi K, Ikawa M, Yamamura O, Fujita Y; Kuriyama M, Nakamoto Y, Rho-kinase ROCK inhibitors reduce oligomeric tau protein. Neurobiology of Aging; 2020; 89: 41-54.

Hou Y, Zhou L, Yang QD, Du XP, Li M, Yuan M, Zhou ZW, Changes in hippocampal synapses and learning-memory abilities in a streptozotocin-treated rat model and intervention by using fasudil hydrochloride. Neuroscience. 2012; 200: 120-129.

Jacobs M, Hayakawa K, Swenson L, Bellon S, Fleming M, Taslimi P, Doran J, The structure of dimeric ROCK I reveals the mechanism for ligand selectivity. J Biol Chem. 2006; 281(1): 260-68.

Kamei S, Oishi M, Takasu T. 1996a. Evaluation of fasudil hydrochloride treatment for wandering symptoms in cerebrovascular dementia with 31P-magnetic resonance spectroscopy and Xe-computed tomography. Clin Neuropharmacol. 19:428-38.

Kamei S, Toshiaki T, Oishi M, Effect of fasudil hydrochloride on wandering symptoms of c cerebrovascular dementia patients. Neurotherapy. 1996b 13:43-50.

Nair & Jacob, A simple practice guide for dose conversion between animals and human. *J Basic Clin Pharm.* 7:27-31 (2016).

Nakagawa O, Fukisawa K, Ishizaki T, Saito Y, Nakao K, Narumiya S, ROCK-I and ROCK-II, two isoforms of Rho-associated coiled-coil forming protein serine/threonine kinase in mice. FEBS Lett. 1996 Aug 26;392(2):189-93.

Nakaoka A, Suto S, Makimoto K, Yamakawa M, Shigenobu K, Tabushi K. 2010. Pacing and lapping movements among institutionalized patients with dementia. Am J Alzheimers Dis Other Demen. 25:167-72.

Román GC, Tatemichi TK, Erkinjuntti T, Cummings JL, Masdeu JC, Garcia JH, Amaducci L, Orgogozo JM, Brun A, Hofman A, et al. 1993. Vascular dementia: diagnostic criteria for research studies. Report of the NINDS-AIREN International Workshop. Neurology. 43:250-60.

Sasaguri H, Nilsson P, Hashimoto S, Nagata K, Saito T, De Snooper B, Hardy J, Vassar R, Winblad B, Saido TC, APP mouse models for Alzheimer's disease preclinical studies. EMBO J. 2017; 36(17): 2473-2487.

Sellers K, Elliott C, Jackson J, Ghosh A, Ribe E, Rojo A, Jarosz-Griffiths HH, Watson AA, Xia W, Semenov M, Morin P, Hooper N, Porter R, Preston J, Al-Shawi R, Baillie G, Lovestone S Cuadrado A, Harate M, Simons P, Srivastava DP, Killick R, Amyloid β synaptotoxicity is Wnt-PCP dependent and blocked by fasudil. Alzeimer's & Dementia. 2018; 14: 306-317.

Shibuya M, Asano T, Sasaki Y. 2001. Effect of Fasudil HCl, a protein kinase inhibitor, on cerebral vasospasm. Acta Neurochir Suppl. 77:201-4.

Turk M. The Effect of Rho Kinase Inhibitors on Alzheimer's Disease, Dissertation. Arizona State University. May 2017.

Uehata M, Ishizaki T, Satoh H, Ono T, Kawahara T, Morishita T, Tamakawa H, Yamagami K, Maekawa M, Narumiya S, Calcium sensitization of smooth muscle mediated by a Rho-associated protein kinase in hypertension. Nature. 1997 Oct 30;389(6654):990-4.

Wetterling T, Kanitz RD, Borgis KJ. 1996. Comparison of different diagnostic criteria for vascular dementia (ADDTC, DSM-IV, ICD-10, NINDS-AIREN). Stroke. 27:30-6. Wick JY, Zanni GR. Aimless excursions: wandering in the elderly. Consult Pharm. 2006;21(8):608-612, 615-618.

Yamaguchi H, Miwa Y, Kasa M, Kitano K, Amano M, Kaibuchi K, Hakoshima T, Structural basis for induced-fit binding of Rho-kinase to the inhibitor Y-27632. J Biochem. 2006 Sep;140(3):305-11.

Yu J, Gu Q, Yan Y, Yu H, Guo M, Liu C, Song G, Chai Z, Wang Q, Zia B, Zhang H, Jiang Y, Cungen MA, Fausidil improves cognition of APP/PS1 transgenic mice via inhibiting the activation of microglia and shifting microglia phenotypes from M1 to M2. Chin J Cell Mol Immunol. 2017; 33(12): 1585-1593.

The disclosure of each reference set forth herein is incorporated herein by reference in its entirety.

The invention claimed is:

1. method of treating Alzheimer's Disease in patient in need thereof comprising orally administering to a patient suffering from Alzheimer's Disease a pharmacologically effective amount of a fasudil.

2. The method according to claim 1, wherein the fasudil is administered in a dose of at least 60 mg/day.

3. The method according to claim 2, herein the fasudil is administered in a dose of 70 to 140 mg/day.

4. The method according to claim 3, wherein the fasudil is administered in a dose of 90 mg-day.

5. The method according to claim 1, wherein the fasudil is fasudil hydrochloride hemihydrate.

6. The method according to claim 1, wherein the fasudil hydrochloride hemihydrate is administered in a solid dosage form.

7. The method according to claim 5, wherein the fasudil hydrochloride hemihydrate is administered in an immediate release dosage form.

8. The method according to claim 1, wherein the activities of daily living are improved in the patient upon treatment with fasudil.

9. The method according to claim 1, wherein cognition is improved in the patient upon treatment with fasudil.

10. The method according to claim 1, wherein the patient has an MMSE score of≤23.

11. The method according to claim 1, wherein the patient has an CDR-SOB score of≥4.5.

12. The method according to claim 1, wherein the method continues for at least 2 months.

13. The method according to claim 1, wherein the patient is aged 65 years or older.

* * * * *

UNITED STATES PATENT AND TRADEMARK OFFICE
CERTIFICATE OF CORRECTION

| | | |
|---|---|---|
| PATENT NO. | : 11,771,704 B1 | Page 1 of 1 |
| APPLICATION NO. | : 18/175605 | |
| DATED | : October 3, 2023 | |
| INVENTOR(S) | : Thomas MacAllister and Sven Jacobson | |

It is certified that error appears in the above-identified patent and that said Letters Patent is hereby corrected as shown below:

In the Claims

At Column 22, Line 35, in Claim 1, please delete:
"method of treating Alzheimer's disease in patient in"
And insert:
--A method of treating Alzheimer's disease in a patient in--

At Column 22, Line 38, in Claim 1, please delete:
"effective amout of a fasudil"
And insert:
--effective amount of fasudil--

At Column 22, Line 44, in Claim 4, please delete:
"is administered in a dose of 90 mg-day"
And insert:
--is administered in a dose of 90 mg/day--

Signed and Sealed this
Seventh Day of November, 2023

Katherine Kelly Vidal
*Director of the United States Patent and Trademark Office*